(12) United States Patent
Hu

(10) Patent No.: US 10,726,950 B2
(45) Date of Patent: Jul. 28, 2020

(54) METHODS AND SYSTEMS FOR AUTONOMOUS CONTROL OF IMAGING DEVICES

(71) Applicant: Aivitae LLC, Redwood City, CA (US)

(72) Inventor: Bob Sueh-chien Hu, Los Altos Hills, CA (US)

(73) Assignee: Aivitae LLC, Redwood City, CA (US)

( * ) Notice: Subject to any disclaimer, the term of this patent is extended or adjusted under 35 U.S.C. 154(b) by 0 days.

(21) Appl. No.: 16/738,272

(22) Filed: Jan. 9, 2020

(65) Prior Publication Data

US 2020/0168320 A1    May 28, 2020

Related U.S. Application Data

(60) Provisional application No. 62/771,139, filed on Nov. 25, 2018.

(51) Int. Cl.
*G06K 9/00* (2006.01)
*G16H 30/20* (2018.01)
*G06N 3/08* (2006.01)

(52) U.S. Cl.
CPC ............... *G16H 30/20* (2018.01); *G06N 3/08* (2013.01)

(58) Field of Classification Search
None
See application file for complete search history.

(56) References Cited

U.S. PATENT DOCUMENTS

2019/0228298 A1\* 7/2019 Suzuki .................. G06N 3/082

\* cited by examiner

*Primary Examiner* — Atiba O Fitzpatrick
(74) *Attorney, Agent, or Firm* — Pillsbury Winthrop Shaw Pittman LLP

(57) ABSTRACT

Methods and systems are described for autonomous control of imaging devices. In particular, the methods and system described herein may account for the differences in normalization of training data and/or test data. The methods and systems may process images through an additional customization layer, which itself may comprise an artificial neural network. The additional customization layer is trained to normalize data for specific applications and/or differences between subsets of data.

21 Claims, 6 Drawing Sheets

METHODS AND SYSTEMS FOR AUTONOMOUS CONTROL OF IMAGING DEVICES

CROSS-REFERENCE TO RELATED APPLICATION

The application claims priority to U.S. Application 62/771,139, which was filed on Nov. 25, 2018 and is hereby incorporated by reference in its entirety.

FIELD OF THE INVENTION

The invention relates to methods and systems for autonomous control of imaging devices.

BACKGROUND

Advancements in artificial intelligence ("AI") have expanded rapidly and for numerous applications. However, even in view of this rapid expansion, applications geared towards to the control of devices, particularly those that must respond to changes in circumstances, unknown variables, and/or ill-defined user preferences still face many hurdles. For example, in conventional systems, computer learning systems, such as artificial neural networks used for image analysis and other computer vision applications, may be trained based on a training data set. Through this training, the system may classify and make other determinations regarding images in data sets. For example, the artificial neural network may be trained to identify a particular object found in a plurality of images of a training data set. An image (e.g., from a test data set, as opposed to the training data set) may then be processed through the trained artificial neural network, and the trained artificial neural network may output a determination as to whether or not the image includes the object.

SUMMARY

As described herein, data sets may be normalized prior to training the artificial neural network or inputting the image into the artificial neural network. For example, if the artificial neural network is being trained to detect objects in images, the training data set may include images of a labeled object where the position, resolution, and/or other image characteristics of the different labeled objects are kept constant. Likewise, any image input into the trained artificial neural network may be normalized to have the same position, resolution, and/or other image characteristics. However, in some applications, images input into a trained artificial neural network and/or the subsets of the training data set (e.g., received from different sources) may have been normalized in a different way or not at all. Moreover, the differences in the normalization (and/or whether the images have been normalized at all) may be difficult to detect and/or describe.

In view of the aforementioned problems, methods and systems are described herein for autonomous control of imaging devices. In particular, the methods and system described herein may account for the differences in normalization of training data and/or test data. For example, in many cases available, training data may be too limited to train an artificial neural network on only a single subset of the training data set (e.g., with a standard normalization). Alternatively, training a universal artificial neural network (e.g., an artificial neural network trained on all subsets) to account for the differences in the way in which training data is normalized may lead to less precise results than training data normalized in a single way (e.g., based on a single training data set) for test data normalized in the same way. Thus, the lack of, or differences in normalization, may adversely affect overall performance of the system. These problems are only exacerbated in situations featuring other sources of noise and/or in situations in which test data may lack specific features, require semantic labels, and/or need nonlinear adjustments.

To address this issue, the methods and systems may process images through an additional customization layer, which itself may comprise an artificial neural network. The additional customization layer is trained to normalize data for specific applications and/or differences between subsets of data. For example, the system may select and apply the customization layer to address specific normalization issues and/or specific applications. The system may then output, from the artificial neural network and customization layer, an image to be displayed to a user and/or used to control an autonomous imaging device (e.g., either automatically or manually by the user).

Through the use of the customization layer, the system may account for the specific applications and/or variances between subsets of data that are not describable or programmable. For example, the system may normalize test data (e.g., test data having a predetermined amount of image tilt) input into an artificial neural network using a customization layer specific to the data subset of the test data (e.g., specific to the predetermined amount of image tilt), in which the customization layer is built on top of an artificial trained neural network, using normalized training data, and/or training data from a single subset of training data (e.g., featuring a different amount of image tilt). The system may receive the data output from the trained artificial neural network and then process that data through the customization layer (e.g., to account for the differences in image tilt).

Additionally, or alternatively, the system may provide for improvements in autonomous imaging which lacks specific features, requires semantic labels, and/or needs nonlinear adjustments. For example, the system may normalize test data by first processing it through a customization layer (e.g., that features a generative artificial neural network prior to processing the test data through a trained discriminatory artificial neural network). In such cases, the generative artificial neural network may reconstruct portions of an inputted image with missing features, the absence of which may prevent the trained discriminatory artificial neural network from properly classifying objects in the image. In another example, the system may normalize test data by first processing it through a customization layer (e.g., that features a geometric artificial neural network prior to processing the test data through a trained convolutional neural network). In such cases, the information determined based on the geometric artificial neural network (e.g., such as the three-dimensional dimensions of an object in the image) is used by a convolutional neural network to properly classify the object and/or identify the bounds of features of the object. In another example, the system may normalize test data by first processing it through a customization layer that applies non-linear adjustments (e.g., coloring, texture mapping, etc.) to the test data. The adjusted test-data may then be input into an artificial neural network that is trained on non-linearly adjusted data (e.g., trained on objects with the same coloring, texture mapping, etc.).

In some aspects, a system for autonomous control of magnetic resonance imaging devices may comprise of receiving a first image from a first data subset of a plurality of data subsets. For example, the system may receive a first image and generate a pixel array (e.g., a series of matrix blocks, in which each matrix block is a row of data, and which each element within that matrix block is the value of a pixel) based on the first image. The first data subset may comprise a subset of data that is normalized in a particular way. For example, the first subset of data may be constituted of images created from magnetic resonance imaging ("MRI") that are distinguished from other Mill images based on an image tilt.

The system may then label the first image with a known object. For example, the system may label the generated pixel array with the known object. The system may then train an artificial neural network to detect the known object based on the labeled image. In some embodiments, in addition to the system specifying the known object in the labeled image, the system may also specify a characteristic of the first data subset (e.g., the image tilt of images in the first data subset).

Subsequent to training the artificial neural network, the system may receive a second image corresponding to a second data subset of the plurality of data subsets. For example, the system may generate a second pixel array based on the second image. The second data asset may also be comprised of an MRI image, but the MRI image may have a different image tilt than images in the first data subset. In some embodiments, the system may determine the different image tilt based on a label corresponding to the second data subset.

The system may then determine a first customization layer for the trained artificial neural network based on a comparison of the first data subset and the second data subset. For example, the system may determine a difference between the image tilt of the first data subset and the second image set, and the system may apply a customization layer based on that difference. The customization layer may itself be an artificial neural network that is trained on accounting for the difference between the image tilt of the first data subset and the second data subset.

The system may then process the image through the trained artificial neural network and the first customization layer to identify the second image as corresponding to the known object. Because the system processes the second image through the first customization layer, the system may use the artificial neural network that was trained on data in the first subset. Accordingly, the training data available for training the artificial neural network may be increased as the artificial neural network may be trained on data in the first subset, but still be used to classify data in the second subset. Moreover, as the trained artificial neural network does not need to account for images having multiple different tilts, and instead relies on the customization layer to account for differences, the trained artificial neural network is more precise.

The system may then receive an output from the trained artificial neural network and the first customization layer. The output may include an identification of the known object in the second image and may be displayed on a display screen. Additionally or alternatively, the output may be used for autonomous control of an imaging device to adjust the image or to control the imaging device itself (e.g., in order to capture additional images). The use of the customization layer for autonomous control of imaging devices it particularly useful as differences in data subsets (e.g., a difference in tilt) may be difficult for human operators to detect and/or describe, as well as to implement in the autonomous control of imaging devices.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents, unless the context clearly dictates otherwise. In addition, as used in the specification and the claims, the term "or" means "and/or" unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagrams form in order to avoid unnecessarily obscuring the embodiments of the invention.

Figure 1:
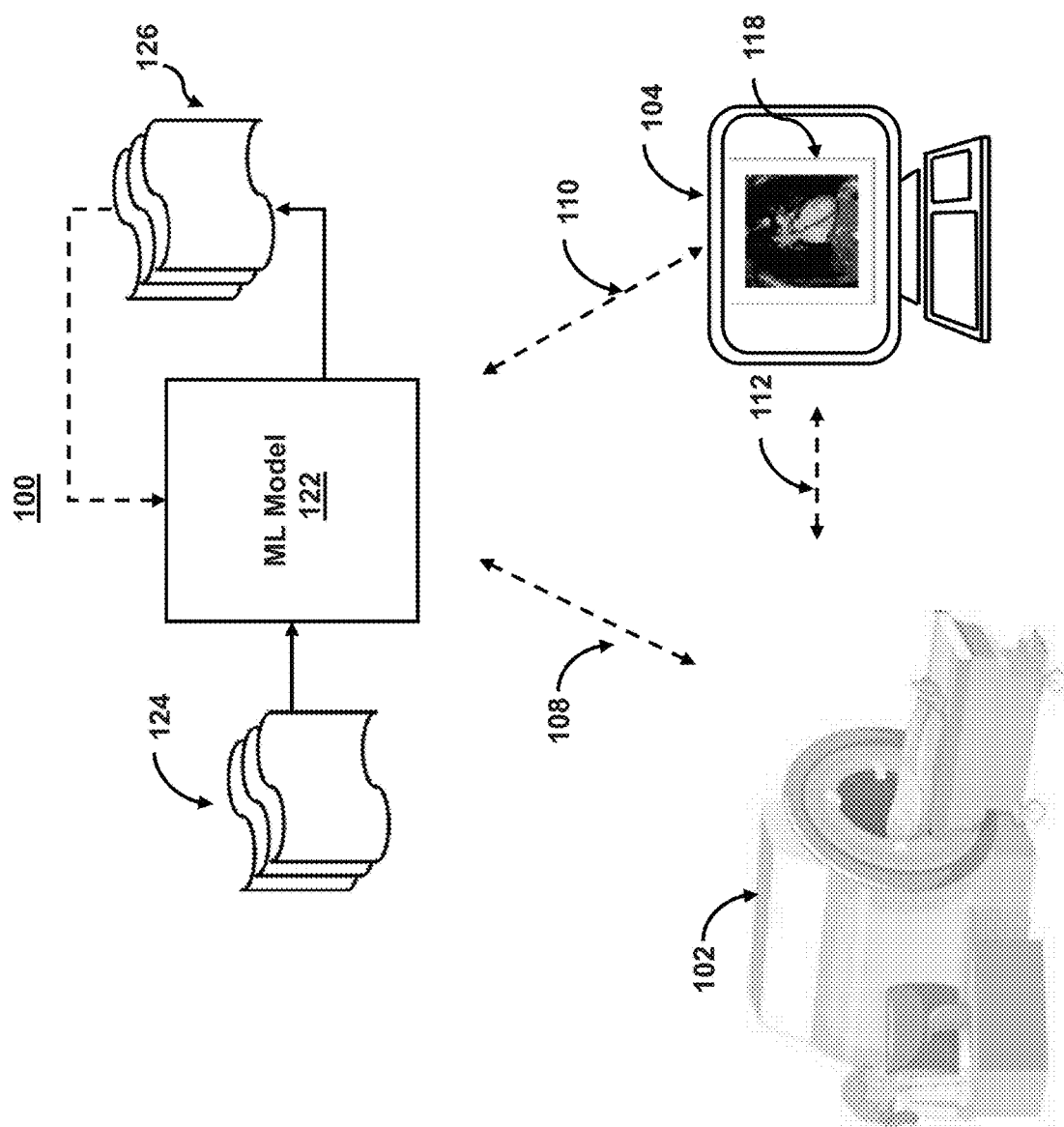
FIG. 1 shows a system diagram for autonomous control of magnetic resonance imaging devices, in accordance with some embodiments.

FIG. 1 shows a system diagram for autonomous control of magnetic resonance imaging devices, in accordance with some embodiments. As shown in FIG. 1, system 100 may include imaging device 102, user terminal 104, and/or other components. Each imaging device, 102 and user terminal 104, may include any type of mobile terminal, fixed terminal, or other device. Each of these devices may receive content and data via input/output (hereinafter "I/O") paths and may also include processors and/or control circuitry to send and receive commands, requests, and other suitable data using the I/O paths. The control circuitry may be comprised of any suitable processing circuitry. Each of these devices may also include a user input interface and/or display for use in receiving and displaying data. By way of example, imaging device 102 and user terminal 104 may include a desktop computer, a server, or other client device. Users may, for instance, utilize one or more of the imaging devices, 102 and user terminal 104, to interact with one another, one or more servers, or other components of system 100. It should be noted that, while one or more operations are described herein as being performed by particular components of system 100, those operations may, in some embodiments, be performed by other components of system 100. As an example, while one or more operations are described herein as being performed by components of imaging device 102, those operations may, in some embodiments, be performed by components of user terminal 104. System 100 also includes machine learning model 122, which may be implemented, or accessible by communication paths 108 and 110, for imaging devices 102 and/or user terminal 104 respectively. It should be noted that, although some embodiments are described herein with respect to machine learning models, other prediction models (e.g., statistical models or other analytics models) may be used in lieu of, or in addition to, machine learning models in other embodiments (e.g., a statistical model replacing a machine learning model and a non-statistical model replacing a non-machine learning model in one or more embodiments).

Each of these devices may also include memory in the form of electronic storage. The electronic storage may include non-transitory storage media that electronically stores information. The electronic storage of media may include (i) system storage that is provided integrally (e.g., substantially non-removable) with servers or client devices and/or (ii) removable storage that is removably connectable to the servers or client devices via, for example, a port (e.g., a USB port, a firewire port, etc.) or a drive (e.g., a disk drive, etc.). The electronic storages may include optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

FIG. 1 also includes communication paths 108, 110, and 112. Communication paths 108, 110, and 112 may include the Internet, a mobile phone network, a mobile voice or data network (e.g., a 4G or LTE network), a cable network, a public switched telephone network, or other types of communications network or combinations of communications networks. Communication paths 108, 110, and 112 may include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

In some embodiments, system 100 may use one or more prediction models for autonomous control of magnetic resonance imaging devices. For example, as shown in FIG. 1, system 100 may identify an object (e.g., object 118) using machine learning model 122, which is displayed on user terminal 104. Additionally or alternatively, system 100 may identify an object (e.g., object 118) and use that identification for autonomous control of imaging device 102. The system may include one or more neural networks (e.g., as discussed in relation to FIG. 3) or other machine learning models.

As an example, with respect to FIG. 1, machine learning model 122 may take inputs 124 and provide outputs 126. The inputs may include multiple data sets such as a training data set and a test data set. Each of the plurality of data sets (e.g., inputs 124) may include data subsets with common characteristics. The common characteristics may include characteristics about how the data was acquired, modified, stored, and/or otherwise handled. For example, these common characteristics may include the identify or location of where the data was collected, the normalization process (if any) for the data, equipment settings and preferences used to generate the data, the number of images taken, the age of the images, the type of object found in the images, etc. The data in each data subset may be labeled with these common characteristics and system 100 may use one or more of these common characteristics to select a machine learning model (e.g., machine learning model 122) or a component thereof (e.g., a customization layer) based on those common characteristics. For example, as described below, system 100 may select a machine learning model featuring a particular customization layer based on a difference in common characteristics corresponding to training and test data sets.

In some embodiments, outputs 126 may be fed back to machine learning model 122 as input to train machine learning model 122 (e.g., alone or in conjunction with user indications of the accuracy of outputs 126, labels associated with the inputs, or with other reference feedback information). In another embodiment, machine learning model 122 may update its configurations (e.g., weights, biases, or other parameters) based on the assessment of its prediction (e.g., outputs 126) and reference feedback information (e.g., user indication of accuracy, reference labels, or other information). In another embodiment, where machine learning model 122 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 122 may be trained to generate better predictions.

Machine learning model 122 may be trained to objects in medical imaging scenarios. For example, imaging device 102 and/or user terminal 104 may generate an image of an object (e.g., via an image capture component of imaging device 102), generate a pixel array based on the image of the object, and/or label the object (or first pixel array). For example, machine learning model 122 may have classifications for various objects that may be encounter in medical imaging scenarios. Machine learning model 122 is then trained based on a first data subset (e.g., data of known objects) to classify an unknown object. Machine learning model 122 may be applied to, but not limited to, imaging using x-rays, computed tomography scans, magnetic resonance imaging, ultrasounds, and/or nuclear medicine imaging, including positron-emission tomography. Accordingly, imaging device 102 may include devices, but not limited to, used for imaging using x-rays, computed tomography scans, magnetic resonance imaging, ultrasounds, and/or nuclear medicine imaging, including positron-emission tomography.

For example, the system may also process images to detect objects. For example, imaging device 102 or user terminal 104 may generate a second pixel array based on an image of the second object and input the second pixel array into machine learning model 122. The system may then receive an output from machine learning model 122 indicating that the second object is the same as the first. For example, the system may input a second image into machine learning model 122. Machine learning model 122 may then classify the objects in the second image. For example, a an organ, portion of an organ, and/or other object may be the first classification of machine learning model 122, and the system may generate an output from machine learning model 122 that the second object is the same based on matching the second pixel array to the first classification.

In some embodiments, system 100 is further configured to perform one or operations based on the output. For example, the system may adjust the settings of imaging device 102, may recapture an image captured with imaging device 102, determine whether or not to capture additional images with imaging device 102, determine whether to capture an image with imaging device 102, and/or other operations associated with medical imaging. It should be noted that while the embodiments described herein are related to medical imaging applications, the embodiments could also be applied to non-medical imaging applications. For example, the embodiments may be applied to any computer vision and/or computer imaging application, particularly those related to the control of autonomous devices (e.g., drones, vehicles, etc.).

Figure 2:
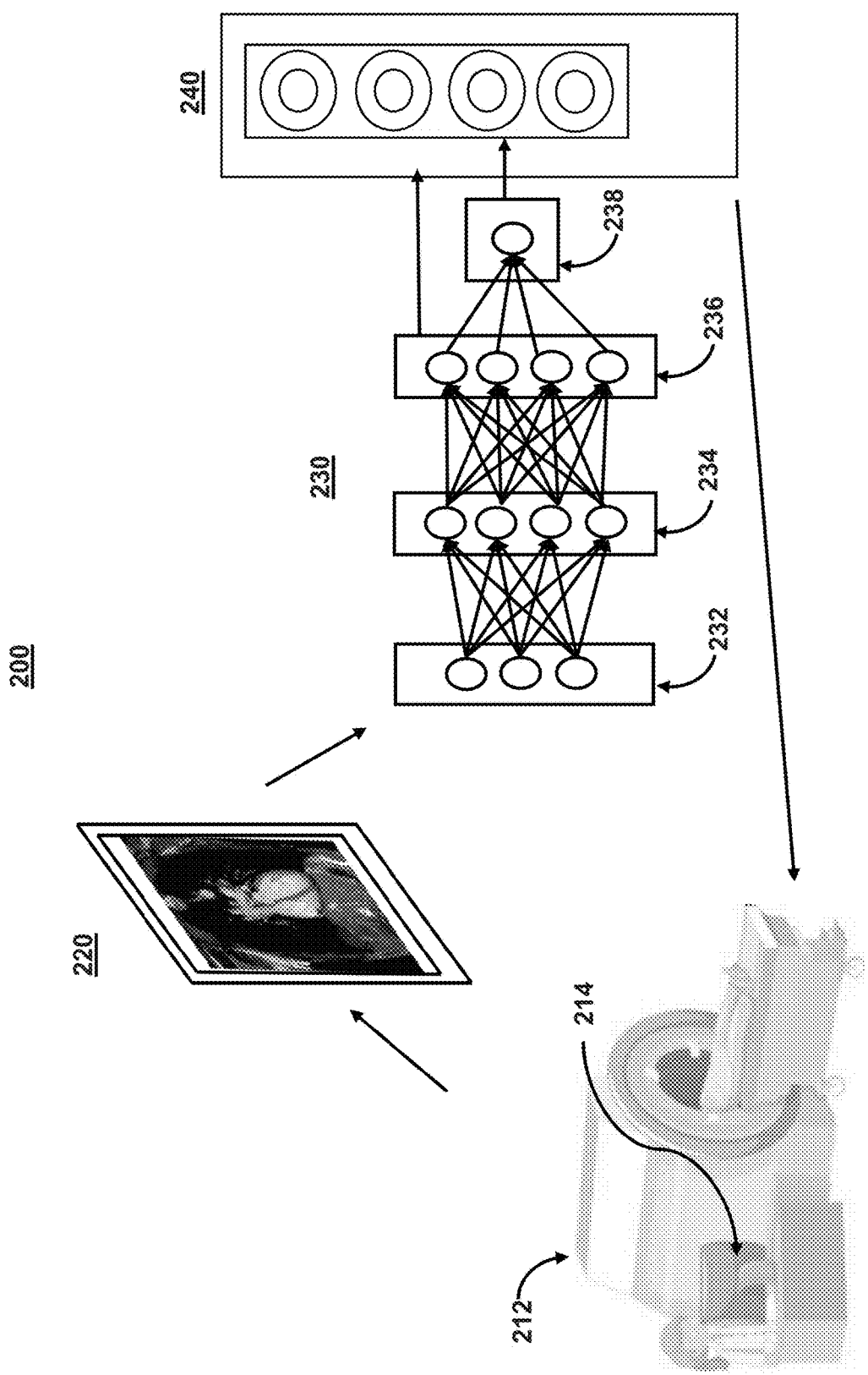
FIG. 2 shows a system diagram for using an artificial neural network and customization layer for autonomous control of magnetic resonance imaging devices, in accordance with some embodiments.

FIG. 2 shows a system diagram for using an artificial neural network and customization layer for autonomous control of magnetic resonance imaging devices, in accordance with some embodiments. System 200 includes imaging device 212 and user terminal 214. In some embodiments, imaging device 212 and user terminal 214 may correspond to imaging device 102 (FIG. 1) and user terminal 104 (FIG. 1), respectively.

As shown in FIG. 2, system 200 has captured image 220 using imaging device 212. System 200 then submits image 220 into an artificial neural network 230. Image 220 is then processed by artificial neural network 230 and the output of artificial neural network 230 is then processed (in series or in parallel) by customization layer 240. The result of artificial neural network 230 and customization layer 240 is then output to imaging device 212. For example, system 200 may display the output (e.g., a modified image of image 220 and/or a verification of an object identified in image 220) on user terminal 214. Additionally or alternatively, system 200 may use the output to adjust imaging device 212.

As shown in FIG. 2, artificial neural network 230 and customization layer 240 are shown as graphical representations of artificial neural network models. For example, artificial neural network 230 and customization layer 240 includes input level 232. System 200 may enter image 220 into artificial neural network 230 at this level. Artificial neural network 230 may also include one or more hidden layers (e.g., hidden layers 232, 234 and 236). Customization layer 240 may also include one or more hidden layers. Each node of artificial neural network 230 or customization layer 240 may be connected with multiple other nodes in artificial neural network 230 or customization layer 240. Through these connections, system 200 can enforce or inhibit the activation state of connected nodes. In some embodiments, each individual node may have a summation function which combines the values of all of its inputs together. In some embodiments, each connection (or the node itself) may have a threshold function that the signal must surpass before it propagates to other node. Artificial neural network 230 and customization layer 240 may be self-learning and trained, rather than explicitly programmed, and can perform significantly better in certain areas of problem solving, as compared to traditional computer programs. During training, output layer 238 may correspond to a classification of artificial neural network 230 (e.g., whether or not image 220 corresponds to a known object) and an input known to correspond to that classification may be input into input layer 232. Likewise, an output layer (not shown) of customization layer 240 may correspond to a classification (e.g., a degree of adjustment to the classification based on the differences between common characteristics of particular data subsets) and an input known to correspond to that classification (e.g., a known adjustment) may be input into an input layer (not shown) of customization layer 240.

In some embodiments, artificial neural network 230 or customization layer 240 may include multiple layers (e.g., where a signal path traverses from front layers to back layers). In some embodiments, back propagation techniques may be utilized by artificial neural network 230 or customization layer 240 where forward stimulation is used to reset weights on the "front" nodes. In some embodiments, stimulation and inhibition for artificial neural network 230 or customization layer 240 may be more free-flowing, with connections interacting in a more chaotic and complex fashion. For example, customization layer 240 may only training particular layers of artificial neural network 230 during the customization process. These layers may result in adapting and determining the artificial neural network 230 to the differences between common characteristics of particular data subsets.

In some embodiments, artificial neural network 230 or customization layer 240 may be a convolutional neural network. A convolutional neural network is an artificial neural network that features one or more convolutional layers. Convolution layers extract features from an input image. Convolution preserves the relationship between pixels by learning image features using small squares of input data, for example, the relationship between the individual parts of image 220.

Customization layer 240 may be comprised of one or more layers, and each layer may be comprised of one or more nodes. Furthermore, system 200 may assign bias and/or weights to a given node and/or layer. The arrangement of layers and the assigned bias and/or weights may correspond to specific applications and/or variances between subsets of data. That is, customization layer 240 may be comprised of various characteristics based on the specific applications and/or differences between subsets of data for which a customization layer is used. Accordingly, system 200 may have access to a plurality of customization layers, each labeled and assigned to a specific application and/or difference between subsets of data.

In some embodiments, system 200 may determine the specific application and/or difference between subsets of data for a given task (e.g., to process image 220, to control imaging device 212, to display an image on user terminal 214, etc.). For each of the specific applications and/or differences between subsets of data, system 200 may retrieve a corresponding customization layer 240. For example, system 200 may input the specific application and/or difference between subsets of data into a database listing customization layers corresponding to specific applications and/or differences between subsets of data. System 200 may then receive an output of a customization layer that corresponds to the input and system 200 may select that customization layer for use.

In FIG. 2, customization layer 240 may correspond to a difference between a subset of data used to train artificial neural network 230 and a subset of data that comprises image 220. For example, during imaging application, multiple factors may affect how image data is collected and stored. For example, during a magnetic resonance imaging ("MM") scan, a user first positions a patient on a table, usually in a supine position. The user then arranges receiver imaging coils around a body part of the patient. The user also identifies a key anatomic structure such as the bridge of the nose or umbilicus as a landmark, which may be correlated with a table position of the patient. The user may then select from a series of imaging protocols, in which each protocol may contain a plurality of pulse sequences oriented in different planes and with different parameter weightings. Next, the user may capture several localizer scans that are used for plotting slices. The user may then calibrate for parallel imaging. The user may then capture slices for the scan. The exact positions and angulation slices will be graphically specified. Additionally, protocol parameters such as field-of-view, directions of phase-encoding and frequency-encoding, and slice thickness, may be modified by the user for the particular patient's anatomy. If saturation bands are required, these are also graphically positioned at this time. Once the slices and bands have been specified and parameters adjusted, imaging device 212 may acquire the images (e.g., image 220).

Slight differences in the variables discussed above, particularly in the positions and angulation slices (e.g., "tilt"), may result in images with slightly different normalization. For example, while the user may also acquire images with the same positions and angulation slices, other users may not. Furthermore, while users in one geographic location (or area of study) may select one set of landmarks, other users in another geographic area may select a different set of landmarks. The resulting images (e.g., image 220) may therefore show the same object, but with slight differences in the positions and angulation slices.

Customization layer 240 accounts for this slight difference. System 200 may determine either automatically or based on a comparison of labels of common characteristics of two data subsets (e.g., the amount of tilt corresponding to each data subset) and may select customization layer 240 to account for that difference. For example, system 200 may include memory configured to store a plurality of data subsets. The first data subset may correspond to images having a first amount of tilt (e.g., having a first position and first angulation slice on an object). System 200 may label the first image as corresponding to the first data subset and/or may label the first image with the common characteristics of the data subset (e.g., the first position and the first angulation slice on the object).

System 200 may then train artificial neural network 230 to identify the object (or features of the object) given the common characteristics. For example, system 200 may train artificial neural network 230 to identify the object (or features of the object) based on an image of the object having the first position and the first angulation slice. In some embodiments, the first data subset may comprise publicly available information from a known third-party source.

System 200 may then receive a second image corresponding to a second data subset of the plurality of data subsets. For example, the second image may correspond to an image captured by imaging device 212. The system may then determine a first customization layer for the trained artificial neural network based on a comparison of the first data subset and the second data subset. For example, the second image may have a different tilt than the first image. The tilt of the second image may correspond to local preferences, settings, and/or regulations of imaging device 212, a user of imaging device 212, and/or a location of imaging device 212. Accordingly, in order to rely on artificial neural network 230, which was trained on images in the first data subset (e.g., having the first position and the first angulation slice of the object), system 200 selects a customization layer to account for the differences between the common characteristics of the first data subset and the second data subset). For example, customization layer 240 may be trained to identify an object (or features of an object) from an image having a second position and second angulation slice of the object based on an image having the first position and the first angulation slice of the object. For example, the customization layer may include a classification that identifies what a known object (or feature of a known object) in an image having the first position and the first angulation slice of the known object appears as in an image, the second position, and the second angulation slice of the object.

Following the determination of customization layer 240, and processing image 220 through artificial neural network 230 and customization layer 240, system 200 may output an instruction to control imaging device 212 and/or generate an image based on the output on user terminal 214.

Figure 3:
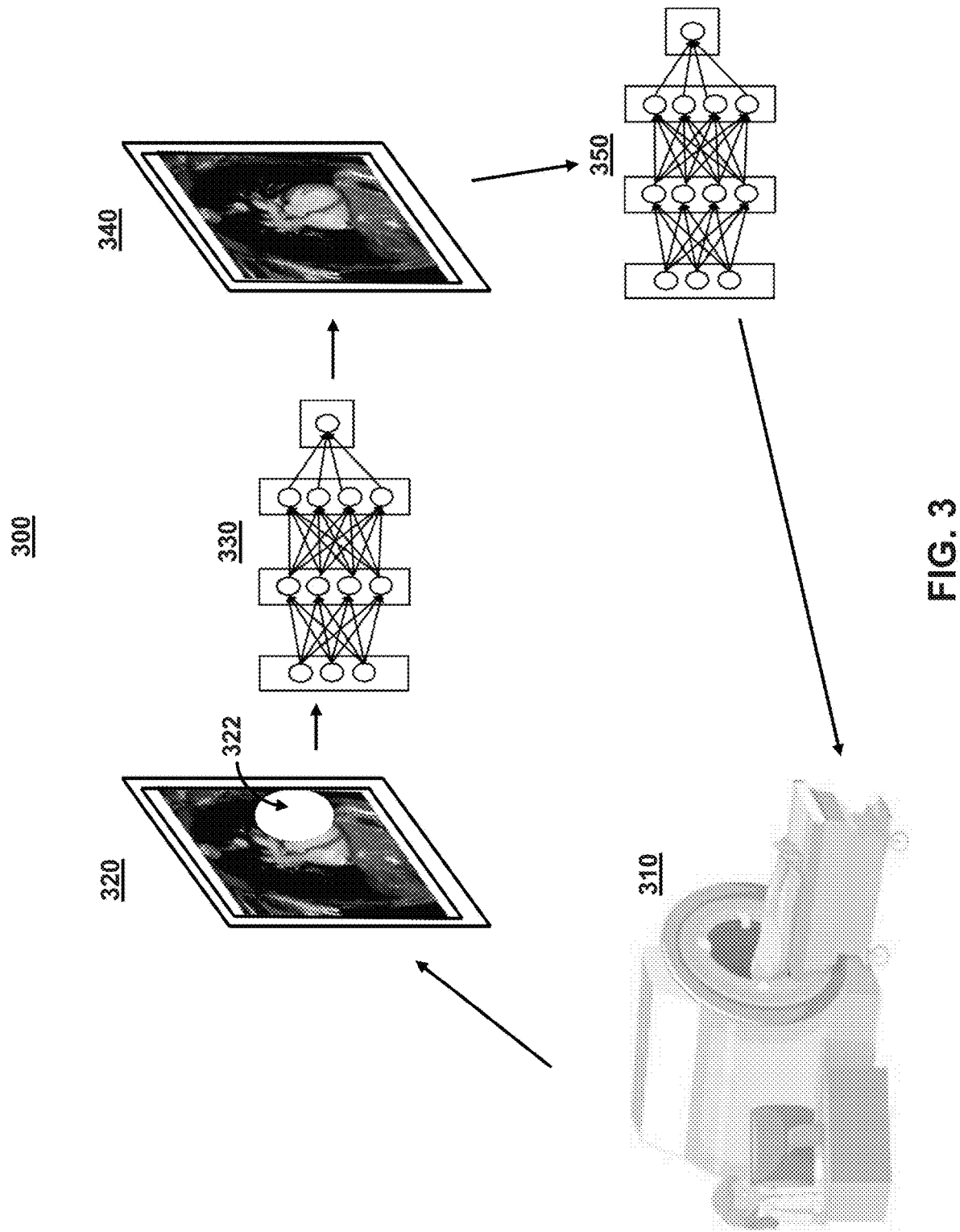
FIG. 3 shows a system diagram for using an artificial neural network and customization layer featuring a generative neural network for autonomous control of magnetic resonance imaging devices, in accordance with some embodiments.

FIG. 3 shows a system diagram for using an artificial neural network and customization layer featuring a generative neural network for autonomous control of magnetic resonance imaging devices, in accordance with some embodiments. In some embodiments, system 300 may be incorporated into system 200 above. For example, image 340 may correspond to image 220 (FIG. 2). As shown in FIG. 3, however, system 300 first applies generative model 330 in order to reconstruct a portion of image 320.

For example, as shown in FIG. 3, system 300 includes imaging device 310. Imaging device 310 may capture image 320. Image 320 is shown with impairment 322. Impairment 322 may include any object, noise, or other condition that obscures and/or distorts an object and/or a feature of an object in an image. For example, impairment 322 may comprise a tumor located near a heart of a user that prevents imaging device 310 from capturing an image of an object in image 320. Despite impairment 322, system 300 still needs to identify objects and/or features of the object in image 320. For example, as discussed in relation to FIG. 2 above, system may need to determine a tilt of image 320 (e.g., a position and an angulation slice of the object). Due to impairment 322, system may not be able to detect landmarks or other marking necessary to identify an object (or process image 320 though artificial neural network 350).

In response, system 300 first processes image 320 through generative model 330. Generative model 330 reconstructs image 320 to remove impairment 322 by determining a likely distribution of features of an object if impairment 322 was not present. For example, as opposed to a discriminate model, which discriminates between different kinds of data instances (e.g., values of pixels to identify an object and/or feature of an object), the generative model of generative model 330 generates new data instances (e.g., values of pixels of an object and/or feature of the object if impairment 322 was not present in image 320).

For example, generative model 330 may identify one or more features in image 320 (e.g., that are identifiable irrespective of impairment 322). Based on the one or more features, generative model 330 determines a likelihood of given values for pixels in image 320 if an impairment in 322 was not present. Based on the determined likelihood of the values for pixels in image 320, generative model 330 outputs image 340. Image 340 corresponds to image 320 without impairment 322.

For example, system 300 may train generative model 330 to identify a value of a pixel in a first image based on other value of pixels, dimensions of identified objects, and/or dimensions of features in the identified objects. For example, system 300 may train generative model 330 to determine values for pixels in one region of the first image based on values from pixels in another region.

System 300 may then receive a second image (e.g., image 320), a portion of which is obscured (e.g., by impairment 322). In response to detecting that a portion of the image is obscured and/or detecting impairment 322, system 300 may apply a customization layer. For example, as system 300 has determine that a portion of image 320 is obscured and/or identified an impairment, system 300 selects a customization layer featuring generative model 330.

Generative model 330 may generate a second image (e.g., image 340). For example, the second image may have a pixel values, dimensions, features, and/or objects that are reconstructed based on the pixel values, dimensions, features, and/or objects detectable in image 320. For the portion of image 320 that is obscured, generative model 330 determines the likely pixel values, dimensions, features, and/or objects for the portion. For example, generative model 330 determines likely values for the unknown values (e.g., pixel values, dimensions, features, and/or objects that are obscured in image 320). For example, if image 320 displays a left ventricle, but the rest of the image is obscured, system 300 may determine that a right ventricle is likely present.

Figure 4:
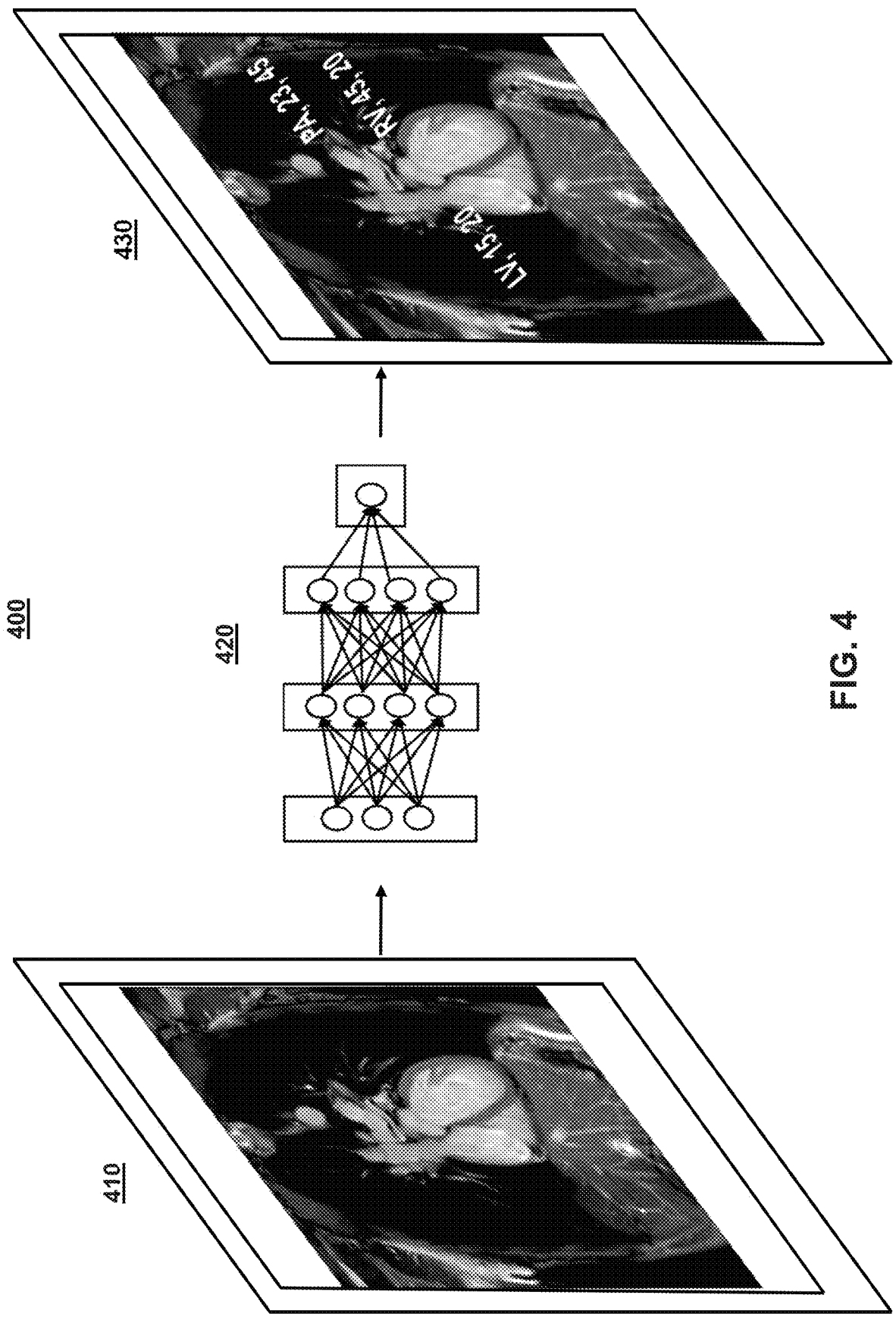
FIG. 4 shows a system diagram for using an artificial neural network and customization layer featuring a geometric neural network for autonomous control of magnetic resonance imaging devices, in accordance with some embodiments.

FIG. 4 shows a system diagram for using an artificial neural network and customization layer featuring a geometric neural network for autonomous control of magnetic resonance imaging devices, in accordance with some embodiments. As shown in FIG. 4, system 400 may apply a customization layer in order to generate semantic features (e.g., labels and/or locations) on an image. For example, system 400 has processed image 410 through customization layer 420 in order to generate image 430, which includes semantic elements (e.g., textual labels applied to the image).

Customization layer 420, may, in some embodiments, may be comprised of a geometric neural network ("GNN"). In the GNN, customization layer 420 may be comprised of nodes that function as multi-directional points and process non-Euclidean data subsets (e.g., graphs and three-dimensional objects). Through the use of the GNN, system 400 may generate three-dimensional views based on image 410. For example, system 400 may determine a three-dimensional view of an object in image 410 based on the position and dimension of features and objects in image 410. System 400 may then determine a three-dimensional model of an object in image 410 based on matching the features and/or objects shown in image 410 to known three dimensional objects having those features and/or objects. For example, based on image 410, the system may determine that an object in image 410 (e.g., a heart organ) has a left ventricle of a given size. System 400 may further determine that image 410 is a front perspective view. System 400 may compare the given size of the left ventricle in image 410 from the front perspective view to front perspective views of known three-dimensional images to determine a three-dimensional image that has a left ventricle of the given size. In response to the match, system 400 may determine that the object in image 410 has the same three-dimensional features as the known match.

System 400 may further determine three-dimensional features to apply semantic elements to image 430. For example, system 400 may indicate the depth and volume of features and/or objects in image 430. For example, in response to a user request (e.g., via imaging device 212 (FIG. 2)) for semantic feature related to three-dimensions, system 400 may selection a customization layer that includes a GNN (e.g., customization layer 420).

Customization layer 420 may include a GNN that is trained on known three-dimensional objects. For example, GNN may be trained to identify a three-dimensional representation of an object based on positions and dimensions of features and objects in an image (e.g., image 410). In such cases, classifications for the GNN may include known three-dimensional models of a given object.

For example, system 400 may train customization layer 420 to identify a value of a pixel in the first image based on other values of pixels, dimensions of identified objects, and/or dimensions of features in the identified objects. For example, system 400 may train customization layer 420 to determine values for pixels in one region (e.g., the far-side of an object that is not viewable in the image) of the first image based on values for pixels in another region (e.g., the near-side of an object that is viewable in the image) of the first image. That is, customization layer 420 may identify three-dimensional models of a given object based on a two-dimensional image. System 400 may then receive an image (e.g., image 410). In some embodiments, system 400 may also receive a request for three-dimensional modeling or three-dimensional based semantic features. In response, system 400 may apply customization layer 420.

Customization layer 420 may generate a second image (e.g., image 430). For example, customization layer 420 may generate a second image (e.g., image 430) that has pixel values, dimensions, features, and/or objects in a three-dimensional model based on the pixel values, dimensions, features, and/or objects detectable in the two-dimensional image (e.g., image 410). For the three-dimensional model of image 410, customization layer 420 determines the likely pixel values, dimensions, features, and/or objects for the portion. For example, customization layer 420 determines likely values for the unknown values (e.g., pixel values, dimensions, features, and/or objects of the three-dimensional model). The system may then generate semantic elements that describe the features (e.g., as an image on user terminal 214 (FIG. 2)) and/or use the three-dimensional model to control an autonomous imaging device (e.g., imaging device 212 (FIG. 2)).

Figure 5:
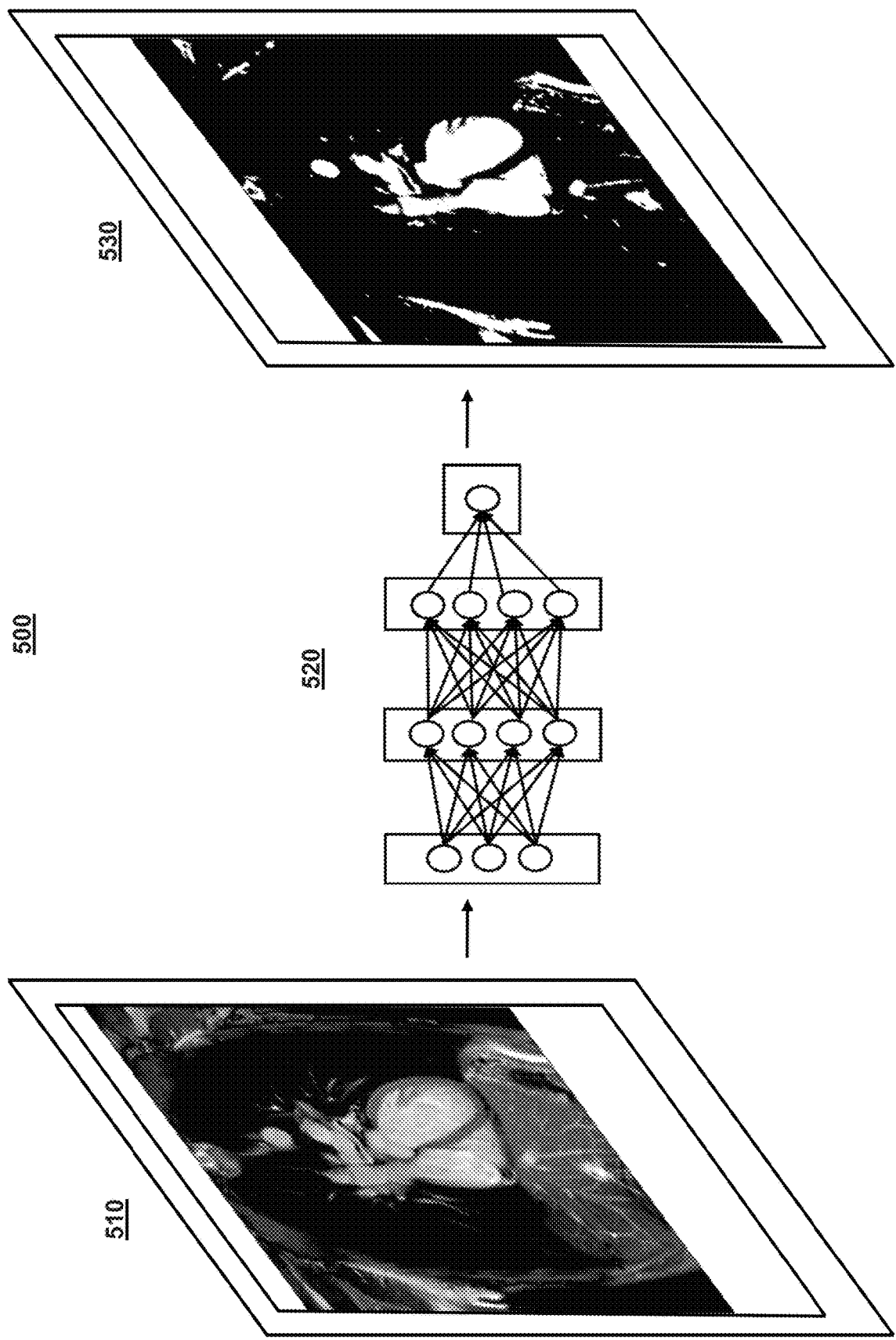
FIG. 5 shows a system diagram for using an artificial neural network and customization layer that provides non-linear adjustments for autonomous control of magnetic resonance imaging devices, in accordance with some embodiments.

FIG. 5 shows a system diagram for using an artificial neural network and customization layer feature that provides non-linear adjustments for autonomous control of magnetic resonance imaging devices in accordance with some embodiments. For example, system 500 may use customization layer 520 to make non-linear adjustments to pixels, objects, and features of objects to generate a modified image (e.g., image 530). The modified image (e.g., image 530) may then be displayed on a user terminal (e.g., user terminal 214

(FIG. 2)) or used to control an autonomous imaging device (e.g., imaging device 212 (FIG. 2)).

For example, system 500 may apply non-linear adjustments to pixels, features, and objects in image 510 in order to represent different contrast, textures, colors, etc. As opposed to linear adjustments, which may have a single potential output, non-linear adjustment may have multiple outputs. Accordingly, a change to an output is not proportional to change in the input. FIG. 5 shows an example of a non-linear adjustment to an image. As shown in FIG. 5, the visual characteristics of image 530 relative to image 510 have been modified. The visual characteristics that may be modified include, but not limited to, color, shade, contrast, brightness, etc. The system may modify the visual characteristics based on texture characteristics of pixels, features, and/or object in an image. Texture characteristics may include the appearance and/or consistency of a surface.

For example, system 500 may train customization layer 520 to identify a value of a visual characteristic in a pixel for the first image based on texture characteristics of pixels, features, or objects in the image. For example, system 500 may train customization layer 520 to determine values for pixels related to a texture based on values for pixels having a similar texture. For example, customization layer 520 may identify a texture of a given object based on visual characteristics of the given object. System 500 may then receive an image (e.g., image 510). In some embodiments, system 500 may also receive a request for non-linear adjustments. In response, system 500 may apply customization layer 520.

Customization layer 520 may generate a second image (e.g., image 530). For example, customization layer 520 may generate a second image (e.g., image 530) that has pixel values that correspond to the color or texture of similar objects upon which customization layer 520 was trained.

Figure 6:
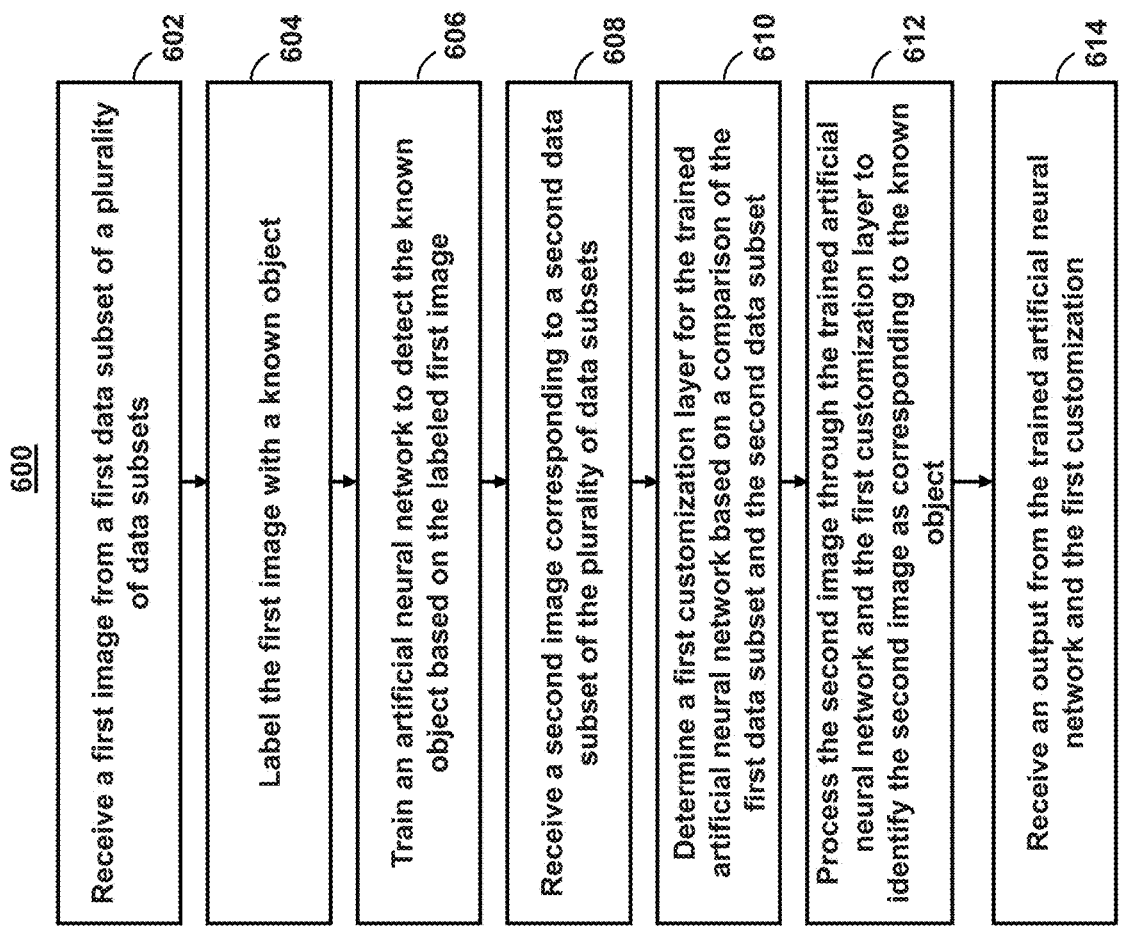
FIG. 6 shows a flowchart of illustrative steps for using an artificial neural network and customization layer for autonomous control of magnetic resonance imaging devices, in accordance with some embodiments.

FIG. 6 shows a flowchart of illustrative steps for using an artificial neural network and customization layer for autonomous control of magnetic resonance imaging devices, in accordance with some embodiments. It should be noted that the steps described below may be performed by any of the devices described in FIGS. 1-3. For example, one or more of the steps below may be performed by imaging device 102 (FIG. 1), machine learning model 122 (FIG. 1), or user terminal 104 (FIG. 1). It should also be noted that the training (e.g., steps 602-606 and testing (e.g., steps 608-614) may comprise separate embodiments. Furthermore, it should be noted that the training steps discussed in relation FIGS. 1-6 may comprise different embodiments that the testing steps. That is, embodiments of this disclosure are not limited to embodiments that include both training and testing and various embodiments may include one or both.

At step 602, process 600 receives (e.g., by control circuitry) a first image from a first data subset of a plurality of data subsets. In some embodiments, each plurality of data subsets may contain images of objects for use in training and testing an artificial neural network. Each plurality of data subsets may also have one or more common characteristics that distinguish one data subset from another. In some embodiments, the system may further generate a first pixel array based on the first image.

At step 604, process 600 labels (e.g., by control circuitry) the first image with a known object. For example, in order to train the artificial neural network, the system may label the first image (or first pixel array) with the known object. The system may also label the first image with a common characteristic (e.g., an amount of tilt in the first image).

At step 606, process 600 trains (e.g., by control circuitry) an artificial neural network to detect the known object based on the labeled first image. For example, the system may train the artificial neural network to classify unknown objects as one or more known objects. In some embodiments, the system may train the artificial neural network on data from a single data subset.

At step 608, process 600 receives (e.g., by control circuitry) a second image corresponding to a second data subset of the plurality of data subsets. For example, images in the second data subset may have one or more common characteristics that distinguish the second data subset from the first data subset. In some embodiments, the system may determine a second pixel array based on the second image.

At step 610, process 600 determines (e.g., by control circuitry) a first customization layer for the trained artificial neural network based on a comparison of the first data subset and the second data subset. For example, the system may compare the common characteristics of the first data subset and the second data subset to determine the difference(s) between the common characteristics. The system may then select the first customization layer based on the first customization layer being trained to account for the difference(s) between the common characteristics.

The system may have a plurality of customization layers from which to select. Each customization layer may be specific to an application and/or task (e.g., to account for the differences between common characteristics of different data subsets). For example, the system may receive a third image corresponding to a third data subset plurality of test data subsets. The system may generate a third pixel array based on the third image. The system may then determine a second customization layer for the trained artificial neural network based on a comparison of the first data subset and the third data subset, process the third pixel array through the trained artificial neural network and the second customization layer. The second customization layer may differ from the first and may have been trained to account for differences between the common characteristics of the first data subset and the third data subset.

At step 612, process 600 develops (e.g., by control circuitry) the second image (or the second pixel area) through the trained artificial neural network and the first customization layer to identify the second image as corresponding to the known object. For example, while the artificial neural network may have been trained on data from the first data subset and the second image is from the second data subset, the system accounts for the differences using the first customization layer to identify the known object.

In some embodiments, when processing the second image (or second pixel array) through the trained artificial neural network and the first customization layer, the system may input the second pixel array into the trained artificial neural network. The system may then receive a preliminary output from the trained artificial neural network, and the system may input the preliminary output from the trained artificial neural network into the first customization layer. For example, the system may first process an image through the artificial neural network and then process the image through the customization layer. By processing the image through the artificial neural network first, the system may identify an object in the image and then apply the customization layer to modify the image for a specific application.

For example, in some embodiments, the comparison of the first data subset and the second data subset indicates a difference in tilt of images from the first data subset and the second data subset (as described in FIG. 2). The system may first identify a known object in an image and then apply the customization layer to account for the difference in tilt in the images. In another example, in some embodiments, the comparison of the first data subset and the second data subset indicates non-linear adjustments in visual characteristics of images from the first data subset and the second data subset, and the output is comprised of a non-linear adjustment to a visual characteristic of the preliminary output. For example, after identifying the object via the trained artificial neural network, the system may modify a visual characteristic of the image as described in FIG. 5.

In some embodiments, wherein processing the second image (or second pixel array) through the trained artificial neural network and the customization layer, the system may input the second pixel array into the first customization layer. The system may then receive a preliminary output from the first customization layer. The system may then input the preliminary output from the first customization layer into the trained artificial neural network. For example, as described in FIG. 2, the system may first process the image through the customization layer to normalize the differences between the first image and the second image, and then identify the object in the second image. In another example, in some embodiments, the first customization layer comprises a generative neural network and the trained artificial neural network is a discriminative neural network. As described in FIG. 3, the system may determine a portion of the known object that is obscured in the second image and generate a version of the second image where the portion is not obscured. That is, the generative neural network may take images that otherwise lack specific features and produce images that can be interpreted by the artificial neural network to execute imaging control instructions. In another example, as described in FIG. 4, the system the first customization layer comprises a geometric neural network and the trained artificial neural network is a convolutional neural network. The system may determine a three-dimensional model of the known object via the customization layer, and then the system may label a feature of the known object in the second image based on the three-dimensional model.

In some embodiments, the system may apply customization layers both before and after processing an image through the trained artificial neural network. For example, in some embodiments, the system may normalize an image both before and after processing the image through the trained artificial neural network. In some embodiments, the system may apply different customization layers (e.g., customization layers directed and different applications of tasks). For example, the system may apply a customization layer as described in FIG. 2 prior to processing the image through a trained artificial neural network, and then process the image through a customization layer as described in FIG. 5.

At step 614, process 600 receives (e.g., by control circuitry) an output from the trained artificial neural network and the first customization. For example, the system may automatically adjust an imaging device (e.g., imaging device 212 (FIG. 2)) based on the output. Additionally or alternatively, the system may display the output on a user terminal (e.g., user terminal 214 (FIG. 2)). In some embodiments, the output may include adjustments to visual characteristics and/or semantic elements (e.g., as discussed in FIGS. 4-5).

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIG. 13 could be used to perform one or more of the steps in FIG. 6.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The present techniques will be better understood with reference to the following enumerated embodiments:

1. A method comprising: receiving a first image from a first data subset of a plurality of data subsets; generating a first pixel array based on the first image; labeling, the first pixel array with a known object; training an artificial neural network to detect the known object based on the labeled first pixel array; receiving a second image corresponding to a second data subset of the plurality of data subsets; generating a second pixel array based on the second image; determining a first customization layer for the trained artificial neural network based on a comparison of the first data subset and the second data subset; processing the second pixel array through the trained artificial neural network and the first customization layer to identify the second pixel array as corresponding to the known object; and receiving an output from the trained artificial neural network and the first customization layer.

2. The method of embodiment 1, further comprising: receiving a third image corresponding to a third data subset of the plurality of test data subsets; generating a third pixel array based on the third image; determining a second customization layer for the trained artificial neural network based on a comparison of the first data subset and the third data subset; and processing the third pixel array through the trained artificial neural network and the second customization layer.

3. The method of embodiment 1 or 2, wherein processing, using the control circuitry, the second pixel array through the trained artificial neural network and the first customization layer, further comprises: inputting the second pixel array into the trained artificial neural network; receiving a preliminary output from the trained artificial neural network; and inputting the preliminary output from the trained artificial neural network into the first customization layer.

4. The method of any one of embodiments 1-3, wherein the comparison of the first data subset and the second data subset indicates a difference in tilt of images from the first data subset and the second data subset, and wherein the output adjusts an imaging device based on the difference.

5. The method of embodiment 4, wherein the comparison of the first data subset and the second data subset indicates non-linear adjustments in visual characteristics of images from the first data subset and the second data subset, and wherein the output comprises a non-linear adjustment to a visual characteristic of the preliminary output.

6. The method of any one of embodiments 1-5, wherein processing, using the control circuitry, the second pixel array through the trained artificial neural network and the customization layer, further comprises: inputting the second pixel array into the first customization layer; receiving a preliminary output from the first customization layer; and inputting the preliminary output from the first customization layer into the trained artificial neural network.

7. The method of embodiment 6, wherein the first customization layer comprises a generative neural network and the trained artificial neural network is a discriminative neural network.

8. The method of embodiment 6, further comprising: determining a portion of the known object that is obscured in the second image; and generating a version of the second image where the portion is not obscured.

9. The method of embodiment 6, wherein the first customization layer comprises a graph neural network and the trained artificial neural network is a convolutional neural network.

10. The method of embodiment 6, further comprising: determining a three-dimensional model of the known object; and labeling a feature of the known object in the second image based on the three-dimensional model.

11. A non-transitory, machine-readable medium storing instructions that, when executed by a data processing apparatus, cause the data processing apparatus to perform operations comprising those of any of embodiments 1-10.

12. A system comprising: one or more processors; and memory storing instructions that, when executed by the processors, cause the processors to effectuate operations comprising those of any of embodiments 1-10.

13. A system comprising means for any of embodiments 1-10.

What is claimed is:

1. A system for autonomous control of magnetic resonance imaging devices, the system comprising:
    memory configured to store a plurality of data subsets; and
    control circuitry configured to:
        receive a first image from a first data subset of a plurality of data subsets;
        generate a first pixel array based on the first image;
        label the first pixel array with a known object;
        train an artificial neural network to detect the known object based on the labeled first pixel array;
        receive a second image corresponding to a second data subset of the plurality of data subsets;
        generate a second pixel array based on the second image;
        determine a first customization layer for the trained artificial neural network based on a comparison of the first data subset and the second data subset;
        process the second pixel array through the trained artificial neural network and the first customization layer to identify the second pixel array as corresponding to the known object;
        receive an output from the trained artificial neural network and the first customization layer; and
        automatically adjust an imaging device based on the output.

2. A method for autonomous control of imaging devices, the method comprising:
    receiving, using control circuitry, a first image from a first data subset of a plurality of data subsets;
    generating, using the control circuitry, a first pixel array based on the first image;
    labeling, using the control circuitry, the first pixel array with a known object;
    training, using the control circuitry, an artificial neural network to detect the known object based on the labeled first pixel array;
    receiving, using the control circuitry, a second image corresponding to a second data subset of the plurality of data subsets;
    generating, using the control circuitry, a second pixel array based on the second image;
    determining, using the control circuitry, a first customization layer for the trained artificial neural network based on a comparison of the first data subset and the second data subset;
    processing, using the control circuitry, the second pixel array through the trained artificial neural network and the first customization layer to identify the second pixel array as corresponding to the known object; and
    receiving, using the control circuitry, an output from the trained artificial neural network and the first customization layer.

3. The method of claim 2, further comprising:
    receiving a third image corresponding to a third data subset of the plurality of data subsets;
    generating a third pixel array based on the third image;
    determining a second customization layer for the trained artificial neural network based on a comparison of the first data subset and the third data subset; and
    processing the third pixel array through the trained artificial neural network and the second customization layer.

4. The method of claim 2, wherein processing, using the control circuitry, the second pixel array through the trained artificial neural network and the first customization layer, further comprises:
    inputting the second pixel array into the trained artificial neural network;
    receiving a preliminary output from the trained artificial neural network; and
    inputting the preliminary output from the trained artificial neural network into the first customization layer.

5. The method of claim 2, wherein the comparison of the first data subset and the second data subset indicates a difference in tilt of images from the first data subset and the second data subset, and wherein the output adjusts an imaging device based on the difference.

6. The method of claim 2, wherein the comparison of the first data subset and the second data subset indicates non-linear adjustments in visual characteristics of images from the first data subset and the second data subset, and wherein the output comprises a non-linear adjustment to a visual characteristic.

7. The method of claim 2, wherein processing, using the control circuitry, the second pixel array through the trained artificial neural network and the first customization layer, further comprises:
    inputting the second pixel array into the first customization layer;
    receiving a preliminary output from the first customization layer; and
    inputting the preliminary output from the first customization layer into the trained artificial neural network.

8. The method of claim 7, wherein the first customization layer comprises a generative neural network and the trained artificial neural network is a discriminative neural network.

9. The method of claim 7, further comprising:
    determining a portion of the known object that is obscured in the second image; and
    generating a version of the second image where the portion is not obscured.

10. The method of claim 7, wherein the first customization layer comprises a geometric neural network and the trained artificial neural network is a convolutional neural network.

11. The method of claim 7, further comprising:
- determining a three-dimensional model of the known object; and
- labeling a feature of the known object in the second image based on the three-dimensional model.

12. A non-transitory, machine-readable medium storing instructions for autonomous control of imaging devices that, when executed by a data processing apparatus, cause the data processing apparatus to perform operations comprising:
- receiving a first image from a first data subset of a plurality of data subsets;
- generating a first pixel array based on the first image;
- labeling the first pixel array with a known object;
- training an artificial neural network to detect the known object based on the labeled first pixel array;
- receiving a second image corresponding to a second data subset of the plurality of data subsets;
- generating a second pixel array based on the second image;
- determining a first customization layer for the trained artificial neural network based on a comparison of the first data subset and the second data subset;
- processing the second pixel array through the trained artificial neural network and the first customization layer to identify the second pixel array as corresponding to the known object; and
- receiving an output from the trained artificial neural network and the first customization layer.

13. The non-transitory, machine-readable medium of claim 12, further comprising instructions that cause the data processing apparatus to perform operations comprising:
- receiving a third image corresponding to a third data subset of the plurality of data subsets;
- generating a third pixel array based on the third image;
- determining a second customization layer for the trained artificial neural network based on a comparison of the first data subset and the third data subset; and
- processing the third pixel array through the trained artificial neural network and the second customization layer.

14. The non-transitory, machine-readable medium of claim 12, further comprising instructions that cause the data processing apparatus to perform operations comprising:
- inputting the second pixel array into the trained artificial neural network;
- receiving a preliminary output from the trained artificial neural network; and
- inputting the preliminary output from the trained artificial neural network into the first customization layer.

15. The non-transitory, machine-readable medium of claim 12, wherein the comparison of the first data subset and the second data subset indicates a difference in tilt of images from the first data subset and the second data subset, and wherein the output adjusts an imaging device based on the difference.

16. The non-transitory, machine-readable medium of claim 12, wherein the comparison of the first data subset and the second data subset indicates non-linear adjustments in visual characteristics of images from the first data subset and the second data subset, and wherein the output comprises a non-linear adjustment to a visual characteristic.

17. The non-transitory, machine-readable medium of claim 12, wherein processing the second pixel array through the trained artificial neural network and the customization layer, further comprises:
- inputting the second pixel array into the first customization layer;
- receiving a preliminary output from the first customization layer; and
- inputting the preliminary output from the first customization layer into the trained artificial neural network.

18. The non-transitory, machine-readable medium of claim 17, wherein the first customization layer comprises a generative neural network and the trained artificial neural network is a discriminative neural network.

19. The non-transitory, machine-readable medium of claim 17, further comprising instructions that cause the data processing apparatus to perform operations comprising:
- determining a portion of the known object that is obscured in the second image; and
- generating a version of the second image where the portion is not obscured.

20. The non-transitory, machine-readable medium of claim 17, wherein the first customization layer comprises a graph neural network and the trained artificial neural network is a convolutional neural network.

21. The non-transitory, machine-readable medium of claim 17, further comprising instructions that cause the data processing apparatus to perform operations comprising:
- determining a three-dimensional model of the known object; and
- labeling a feature of the known object in the second image based on the three-dimensional model.

* * * * *